United States Patent [19]

Lindberg

[11] Patent Number: 4,941,462
[45] Date of Patent: Jul. 17, 1990

[54] ORTHOSIS

[76] Inventor: Ulf Lindberg, Lövhagens Gard, S-170 17 Färentuna, Sweden

[21] Appl. No.: 189,667

[22] Filed: May 3, 1988

[30] Foreign Application Priority Data

May 4, 1987 [SE] Sweden .................. 8701842

[51] Int. Cl.$^5$ ................................. A61F 500
[52] U.S. Cl. ........................ 128/80 C; 128/80 F
[58] Field of Search ............ 128/80 R, 80 C, 80 F, 128/85, 87, 88, 165

[56] References Cited

U.S. PATENT DOCUMENTS

| | | | |
|---|---|---|---|
| 3,318,305 | 5/1967 | Schultz | 128/80 R |
| 3,387,305 | 6/1968 | Shafer | 128/80 R |
| 3,786,804 | 1/1974 | Lewis | 128/80 C |
| 3,817,244 | 6/1974 | Taylor | 128/80 C |
| 4,064,874 | 12/1977 | Valin | 128/80 C |
| 4,084,584 | 4/1978 | Detty | 128/80 C |
| 4,116,236 | 9/1978 | Albert | 128/80 C |
| 4,287,885 | 9/1981 | Applegate | 128/80 C |
| 4,296,744 | 10/1981 | Palumbo | 128/80 C |
| 4,407,276 | 10/1983 | Bledsoe | 128/80 RX |
| 4,697,583 | 10/1987 | Mason et al. | 128/80 F |
| 4,700,698 | 10/1987 | Kleylein | 128/80 C |

Primary Examiner—Robert A. Hafer
Assistant Examiner—Kevin G. Rooney
Attorney, Agent, or Firm—Ostrolenk, Faber, Gerb & Soffen

[57] ABSTRACT

The present invention relates to an orthosis consisting of a sleeve (1) of soft, elastic material, secured on each side of the joint. The orthosis comprises two detachably secured lateral stabilizing splints (8, 9) each of which consists of two arms (10, 11; 12, 13) connected by a pivot joint (14, 15). A Velcro strip is adhered to each arm (10, 11; 12, 13) and cooperates with a corresponding Velcro strip (16, 17) stitched onto the sleeve (1). In order to avoid material-bunching and the formation of folds on the flexing side of the orthosis, a section (18) without any material is provided in this region.

6 Claims, 2 Drawing Sheets

ORTHOSIS

BACKGROUND OF THE INVENTION

The present invention relates to an orthosis for stabilizing a joint, preferably a knee-joint, consisting of a sleeve of a flexible and stabilizing material having a first portion to be secured on one side of the joint and a second portion to be secured on the other side of the joint.

The knee is the joint in the human, body which is subjected to the greatest load. A relatively large percentage of people suffer from pain and/or other disorders in this joint. Sometimes the cause of the trouble can be diagnosed immediately with the aid of an arthroscope, for instance. The cause may be rheumatoidal changes, often including the decomposition of the joint cartilage. Often, however, no immediate cause of the pain can be detected.

The treatment of PFPS (Patello Femoral Pain Syndrome) is either surgical or conservative. Surgery should only be resorted to if the cause of the problem has been clearly diagnosed. The most usual conservative treatment comprises providing the knee with lateral support, using various forms of elastic bandages and orthoses and in all cases the pain is alleviated and increased bending ability is observed in the joint.

As to long-term effects, a definite improvement is obtained if the orthosis includes a patella bracing pad, a halfmoon-shaped cushion, which is in constant contact with one side of the kneecap. The reason for the beneficial effect of the patella bracing pad is still not fully established.

One drawback of existing orthoses is that they are uncomfortable to wear, particularly the type most effective from the treatment aspect, i.e. including a patella bracing pad. The discomfort is due to folds occurring in the material in the crook of the knee when the knee-joint is bent. It is also probable that this material-bunching when the knee is bent gives poorer treatment results.

One solution to this problem would be to provide the orthosis with a recess on the knee-crook side, just as most knee orthoses having an opening for the kneecap (patella). However, in traditional orthoses such a measure is impossible since this greatly reduces stability and thus the efficacy of the treatment.

SUMMARY OF THE INVENTION

The object of the invention is to achieve an orthosis in which the above-mentioned formation of folds in the material in the crook of the knee is eliminated, but in which the stability is at least comparable to that of conventional orthoses.

This is achieved in that the orthosis comprises stabilizers to increase lateral bending stability of the sleeve and in that the sleeve is provided in the region where the joint flexes, with a section either entirely without material or of considerably thinner material than the rest of the sleeve.

The orthosis preferably includes a pocket to receive a patella bracing pad for stabilizing the patella.

In this case the patella bracing pad is suitably provided with tapes to position it securely in a stabilizer.

One embodiment of the invention is described hereafter with reference to the accompanying drawings in which

DETAILED DESCRIPTION OF THE DRAWINGS

Figure 1:
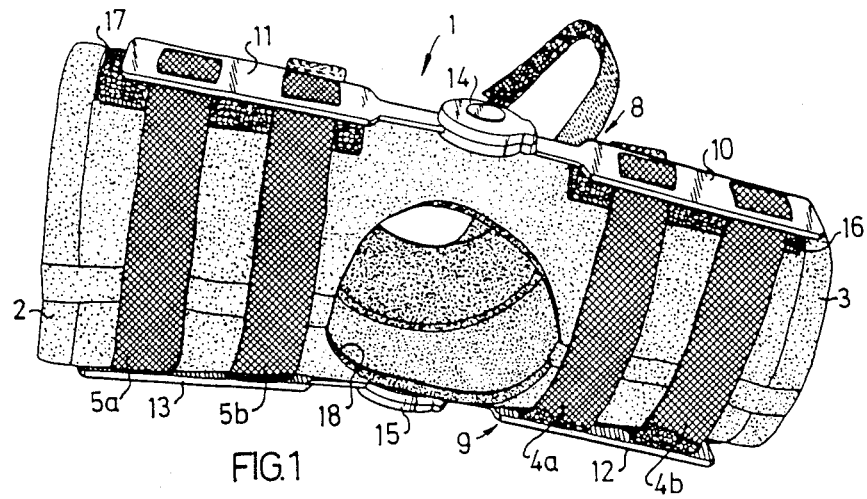
FIG. 1 shows in perspective an orthosis according to the invention, seen from the rear.
Figure 2:
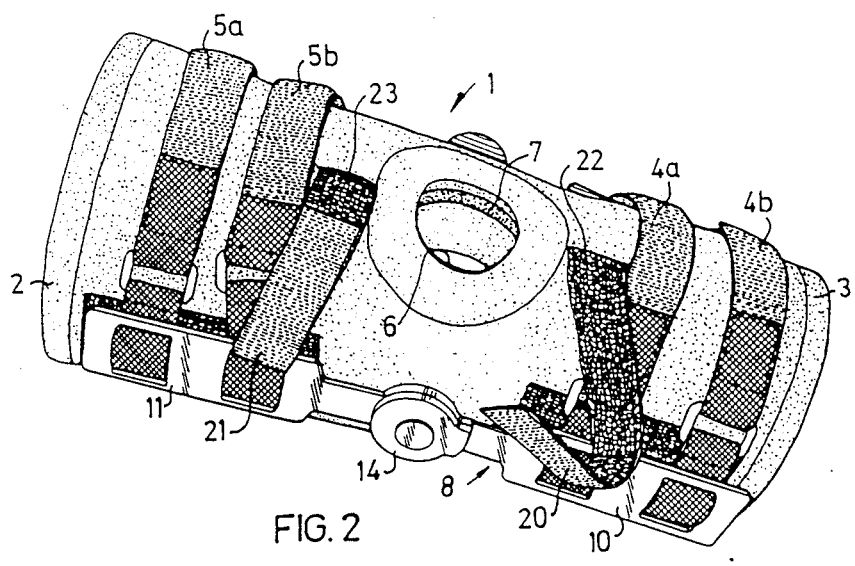
FIG. 2 shows in perspective the orthosis of FIG. 1 seen at an angle from the front.

The orthosis 1 shown in FIGS. 1 and 2 is designed for use on a knee-joint and consists of a sleeve comprising an upper portion 2 which is applied around the lower part of the thigh, and a lower portion 3 which fits around the upper part of the lower leg.

The sleeve material is relatively soft and preferably somewhat elastic so that it fits well around the regions in the vicinity of the knee.

Straps 4a, 4b and 5a, 5b, respectively, are provided which can be steplessly tightened with the aid of securing strips of the type marketed under the registered trademark Velcro (hereinafter "Velcro ® type securing strips") in order to regulate the tension around the thigh and lower leg, respectively. The lower-leg section 3 and the thigh section 2 is each provided with two straps 4a, 4b and 5a, 5b, respectively.

An opening 6 is provided centrally in the orthosis 1 for the kneecap.

Figure 3:
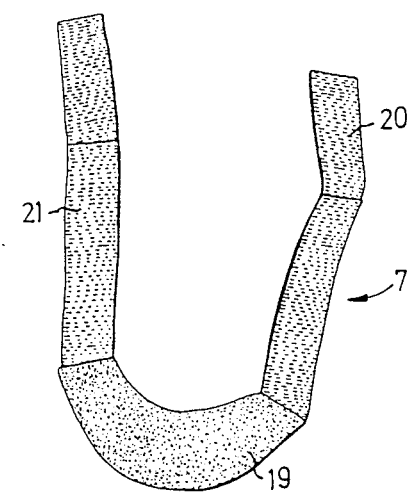
FIG. 3 is a view from above of a patella-bracing pad designed for use with the orthosis shown in FIGS. 1 and 2.

Around this opening 6 is a pocket for a patella bracing pad 7, shown in more detail in FIG. 3.

The construction of the patella bracing pad is described in more detail below.

At each side of the orthosis is a stabilizing splint 8, 9, consisting of two relatively stiff arms 10, 11 and 12, 13, respectively, and a pivot joint 14 and 15, respectively. The pivot joint 14 connects the arms 10 and 11 while the pivot joint 15 connects the arms 12 and 13.

The stabilizing splints 8, 9 are made of a relatively rigid material such as polythene or PVC. The position of the pivot joints 14, 15 corresponds approximately to the bending axis of the knee-joint. In the example shown the splints 8, 9 are detachably secured to the sides of the orthosis by means of Velcro ® type securing strips, a Velcro ® type securing strip being adhered to each arm 10, 11, 12, 13 and cooperating strips 16, 17 being stitched onto the sleeve. The stabilizing splints 8, 9 are provided with attachment means for straps 4a, 4b and 5a, 5b, respectively, and the distance between the splints can be regulated with the aid of these straps.

The lateral stabilizing splints 8, 9 give the orthosis such stability and rigidity that the formation of folds of material in the crook of the orthosis can be avoided. Immediately opposite the opening 6 for the kneecap is a larger, circular opening 18 which prevents any folds being formed in the vicinity of the crook of the knee when the knee-joint is bent.

The patella-bracing pad 7 shown in FIG. 3 is shaped approximately as a half-moon and consists of a pad 19 in contact with one side of the kneecap. At the ends of the pad 19 are tapes 20 and 21, respectively, which are passed through slots 22 and 23, respectively, in the orthosis. The positioning tapes 20, 21 are then secured to the stabilizing splint 8, the positioning tape 20 to arm 10 and the positioning tape 21 to arm 11. The patella bracing pad thus has an accurately defined position relative to the stabilizing splint 8 throughout the bending region of the orthosis. The positioning tapes 20, 21 are provided with Velcro ® type securing strips, allowing the position of the patella bracing pad 7 to be adjusted steplessly relative the splint 8.

By securing the pad tapes to the stabilizer splint, the pad tapes do not have to extend around the knee and be fixed to the opposite end of the pad in order to stabilize the pad. Hereby the pad tapes will not press against the crook of the knee and cause discomfort.

The orthosis described here by way of example may of course be varied in many ways. For instance, not all the material behind the knee need be removed. In certain cases it may be sufficient if the material is thinner in this region, so that folds are not produced to any great extent.

Furthermore, the example relates to a knee-joint, for which the orthosis is particularly suitable. However, the inventive concept is also applicable to other types of orthosis such as orthoses for the elbow.

I claim:

1. An orthosis for stabilizing a joint comprising:
   a sleeve of a flexible and stabilizing material having a first portion to be secured on one side of the joint and a second portion to be secured on the other side of the joint;
   at least one stabilizer for increasing a lateral bending stability of the sleeve, the stabilizer comprising at least one laterally arranged, two-armed stabilizing splint in which the arms of the splint are connected via a pivot joint, the sleeve being provided in the region where the joint flexes, with a section which is entirely without material;
   a patella bracing pad designed to abut the kneecap, the patella bracing pad being adjustably positionable relative to the stabilizer and the patella bracing pad being provided with tapes and the tapes being securable to the stabilizer, the patella pad being adapted to be placed on the inner side of the sleeve to abut the kneecap; and
   through-openings in the sleeve, the tapes of the patella bracing pad passing through the through-openings and the free ends thereof being securable to the stabilizer.

2. An orthosis as claimed in claim 1, wherein the stabilizing splint is detachably connected to the sleeve.

3. An orthosis as claimed in claim 2, wherein the stabilizing splint is detachably connected to the sleeve by means of hook and loop type securing strips.

4. An orthosis as claimed in claim 1, wherein said at least one stabilizer comprises first and second stabilizers and each of said first and second stabilizers comprises its own respective laterally arranged, two-arm stabilizing splint in which the arms of the splint are connected via a pivot joint.

5. An orthosis as claimed in claim 1, wherein the joint is a knee-joint.

6. An orthosis for stabilizing a joint, comprising:
   a sleeve of a flexible and stabilizing material having a first portion to be secured on one side of the joint and a second portion to be secured on the other side of the joint;
   at least one stabilizer for increasing a lateral bending stability of the sleeve, the stabilizer comprising at least one laterally arranged, two-armed stabilizing splint in which the arms of the splint are connected via a pivot joint, the sleeve being provided in the region where the joint flexes with a section which is made of a material which is considerably thinner than the thickness of the material in the rest of the sleeve;
   a patella bracing pad designed to abut the kneecap, the patella bracing pad being adjustably positionable relative to the stabilizer and the patella bracing pad being provided with tapes and the tapes being securable to the stabilizer, the patella pad being adapted to be placed on the inner side of the sleeve to abut the kneecap; and
   through-openings in the sleeve, the tapes of the patella bracing pad passing through the through-openings and the free ends thereof being securable to the stabilizer.

* * * * *